United States Patent [19]

Howlett

[11] 4,151,742
[45] May 1, 1979

[54] HIGH VOLUME AIR SAMPLER

[75] Inventor: Charles L. Howlett, Lyndhurst, Ohio

[73] Assignee: Medusa Corporation, Shaker Heights, Ohio

[21] Appl. No.: 850,772

[22] Filed: Nov. 11, 1977

[51] Int. Cl.² .............................................. G01N 1/24
[52] U.S. Cl. ...................................................... 73/28
[58] Field of Search ............................. 73/28, 421.5 R

[56] References Cited

U.S. PATENT DOCUMENTS

| | | | |
|---|---|---|---|
| 2,484,202 | 10/1949 | Wintermute | 73/28 |
| 3,104,542 | 9/1963 | Scoggins | 73/28 |
| 3,657,920 | 4/1972 | Teel et al. | 73/28 |

*Primary Examiner*—Charles A. Ruehl
*Attorney, Agent, or Firm*—Cooper, Dunham, Clark, Griffin & Moran

[57] ABSTRACT

The invention relates to a high volume air sampler for sampling particulate matter in an area during a predetermined time period. It provides a structure having a vertically movable roof which may be raised to expose a filter paper during a sampling period and thereafter be lowered to seal the filter paper enclosure at the end of the sampling period. The roof is mounted on drive screws which serve to raise the roof at the start of the sampling period and to lower the roof at the end of the sampling period. A gear reducer and reversible motor serve to turn the drive screws through a chain and sprockets connected to such drive screws. A timer initiates the start of the sampling period and starts the reducer and motor which in turn through the drive screws, chain and sprocket assembly raises the roof of the high volume sampler. When the roof reaches its uppermost position a limit switch turns on a vacuum fan motor which thereby causes particulate to collect on the filter paper. At the end of the pre-set period the gear reducer and motor lower the roof, a second limit switch shuts off the vacuum fan motor, and the roof isolates the filter paper from further particulate fallout.

9 Claims, 9 Drawing Figures

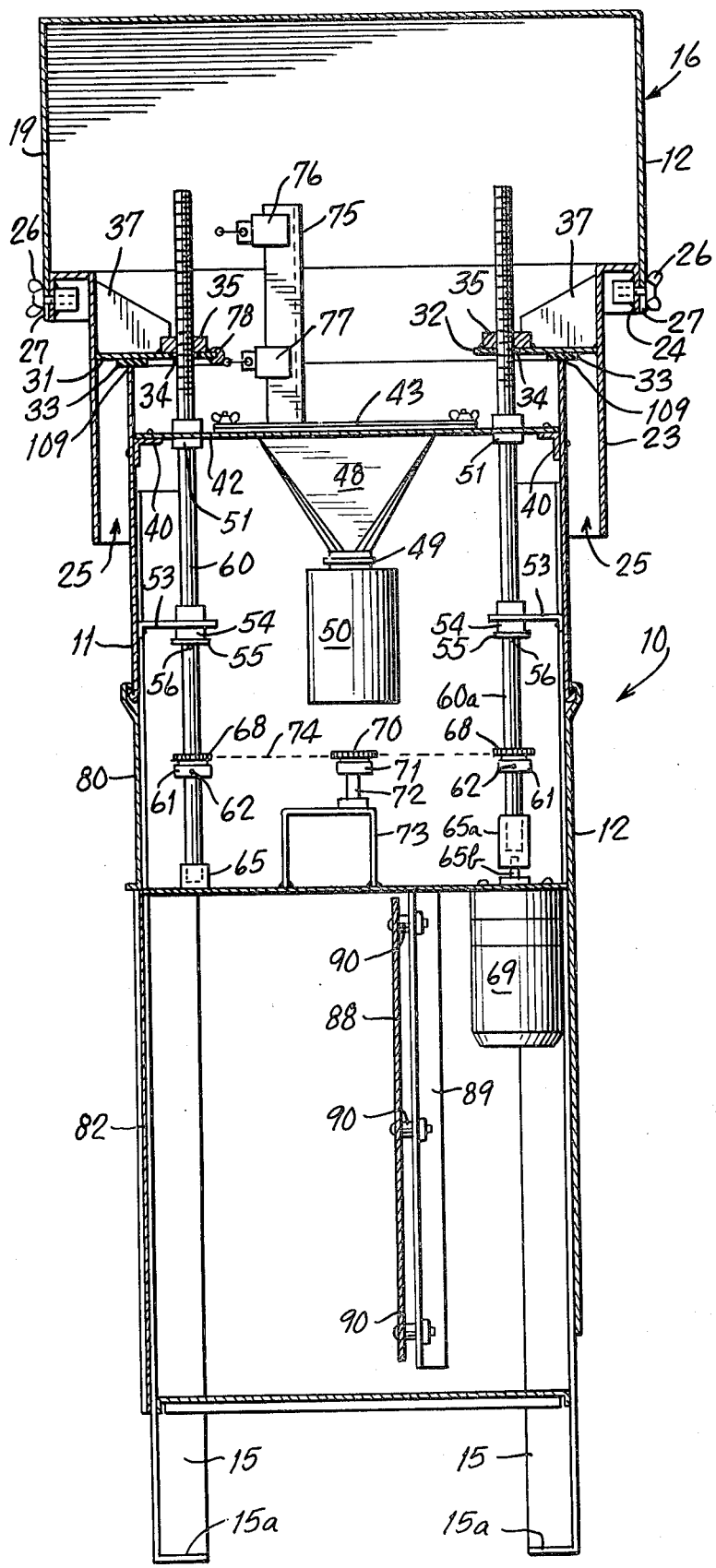
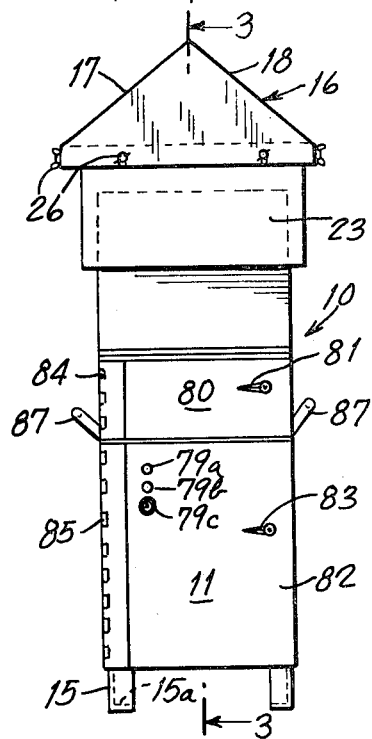
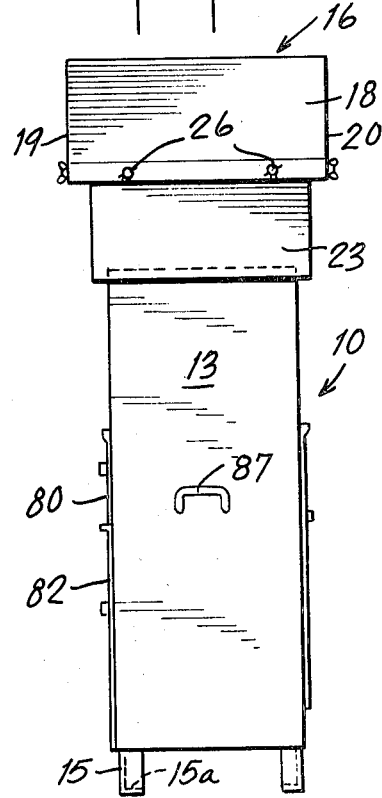

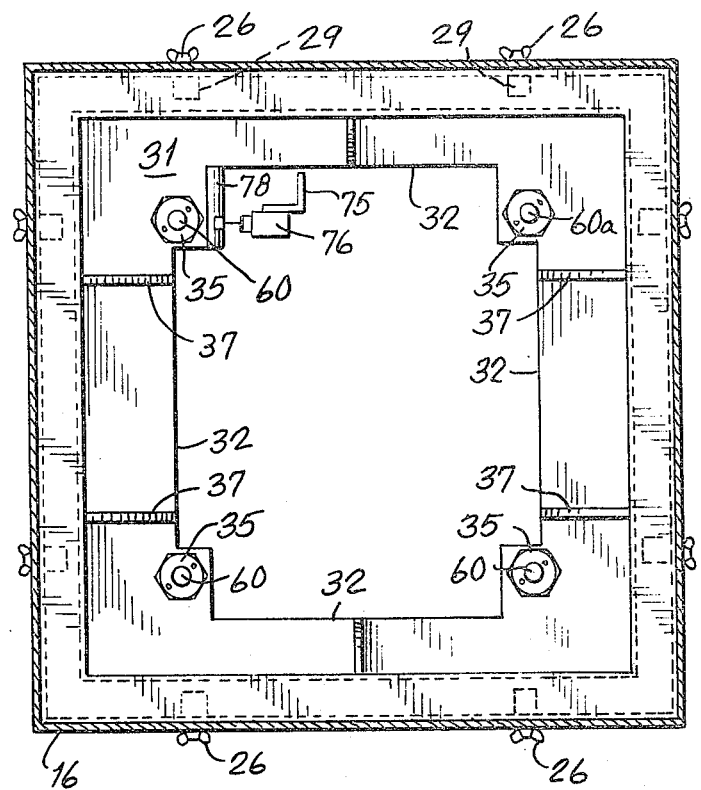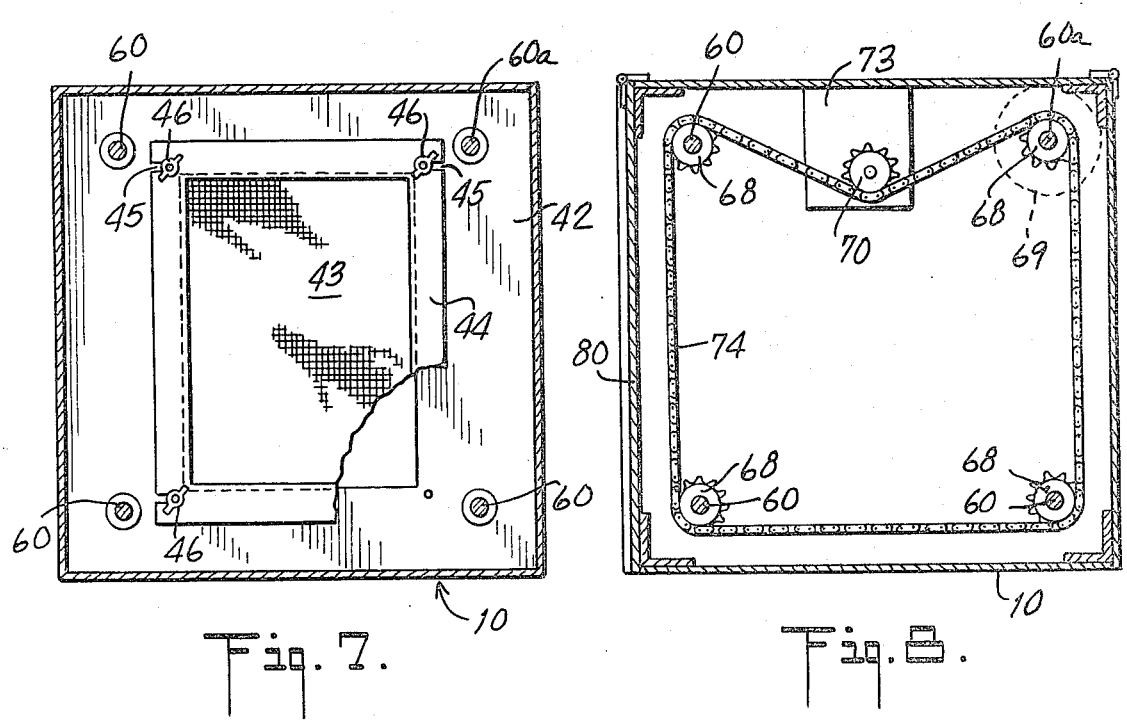

HIGH VOLUME AIR SAMPLER

The present invention relates to a high volume air sampler for sampling particulate matter in an area during a predetermined time period.

According to current practice high volume air samplers are provided with a filter and a vacuum blower. Federal Government criteria for the use of high volume air samplers require that the air be sampled for a 24-hour period every six days. The current procedure is to install filter paper and to set a six-day timer so designed that the vacuum blower will operate for a desired 24-hour period within such six days. At the end of the six day period, the filter paper is removed, a new filter paper is installed, and the timer is reset. In such a six day cycle the filter paper is in position for an average of six days with the blower motor operating for only 24 hours during the entire period.

It is the opinion of applicant that in order to obtain a correct measurement of the particulate fallout with existing high volume air samplers, a new filter paper should be introduced at the startup of the blower and that the filter paper should be removed at the end of the 24-hour period in order to obtain precise data as to particulate fallout. This would obviously require two calls to each monitoring station every six days. This procedure would be economically unsound.

Prior to the development of the present invention it has been found that with high volume air samplers operating on a six-day cycle about 28% of the total particulate falls out on the filter paper when the vacuum blower is not operating. This gives rise to a false reading for the twenty-four hour test period.

According to the present invention the high volume air sampler is so constructed that no particulate can fall out on the filter when the vacuum blower is not operating.

In accomplishing this purpose the high volume sampler of the present invention is provided with a vertically movable roof which may be raised to expose the filter paper during the sampling period and thereafter lowered to seal the same at the end of such sampling period. The filter paper will be exposed for sampling when the roof is raised, preferably for about a 24 hour sampling period. At the end of such period the roof will be lowered to seal off the exposure of the filter paper and the roof will be brought into tight contact with a rubber gasket surrounding the filter paper area to thereby seal the same from further precipitation.

In the present embodiment of the invention the high volume sampler is equipped with a roof mounted on drive screws which serve to raise the roof during the sampling period and to lower the roof to seal the sampling area at the end of such sampling period,—a gear reducer and motor serving to turn the drive screws through a chain and sprockets. A timer initiates the start of the 24 hour sampling period and starts the reducer and motor which in turn through the drive screws, chain and sprocket assembly raises the roof of the high volume sampler. When the roof reaches its uppermost position a limit switch turns on a vacuum fan motor which thereby causes particulate to collect on the filter paper. At the end of the 24 hour preset period the gear reducer and motor will lower the roof, a second limit switch will shut off the vacuum fan motor, and the roof will isolate the filter paper from any further particulate fallout.

For a better understanding of the invention reference is now made to the accompanying drawings wherein:

FIG. 1 is a front elevational view of the high volume air sampler provided by the present invention with the roof in lowered position whereby the filter paper is sealed off from deposit of particulate matter;

FIG. 2 is a side elevational view of the high volume air sampler with the roof in elevated position so that particulate matter can be collected on the filter paper;

FIG. 3 is a longitudinal cross-sectional view taken along the lines 3—3 of FIG. 1 and looking in the direction of the arrows;

FIG. 6 is a horizontal sectional view of the volume air sampler of FIG. 4, taken along the lines 6—6 and viewed in the direction of the arrows;

FIG. 7 is a horizontal cross-sectional view taken along the lines 7—7 of FIG. 4 and viewed in the direction of the arrows;

FIG. 8 is a horizontal cross-sectional view taken along the lines 8—8 of FIG. 4 and viewed in the direction of the arrows.

Figure 4:
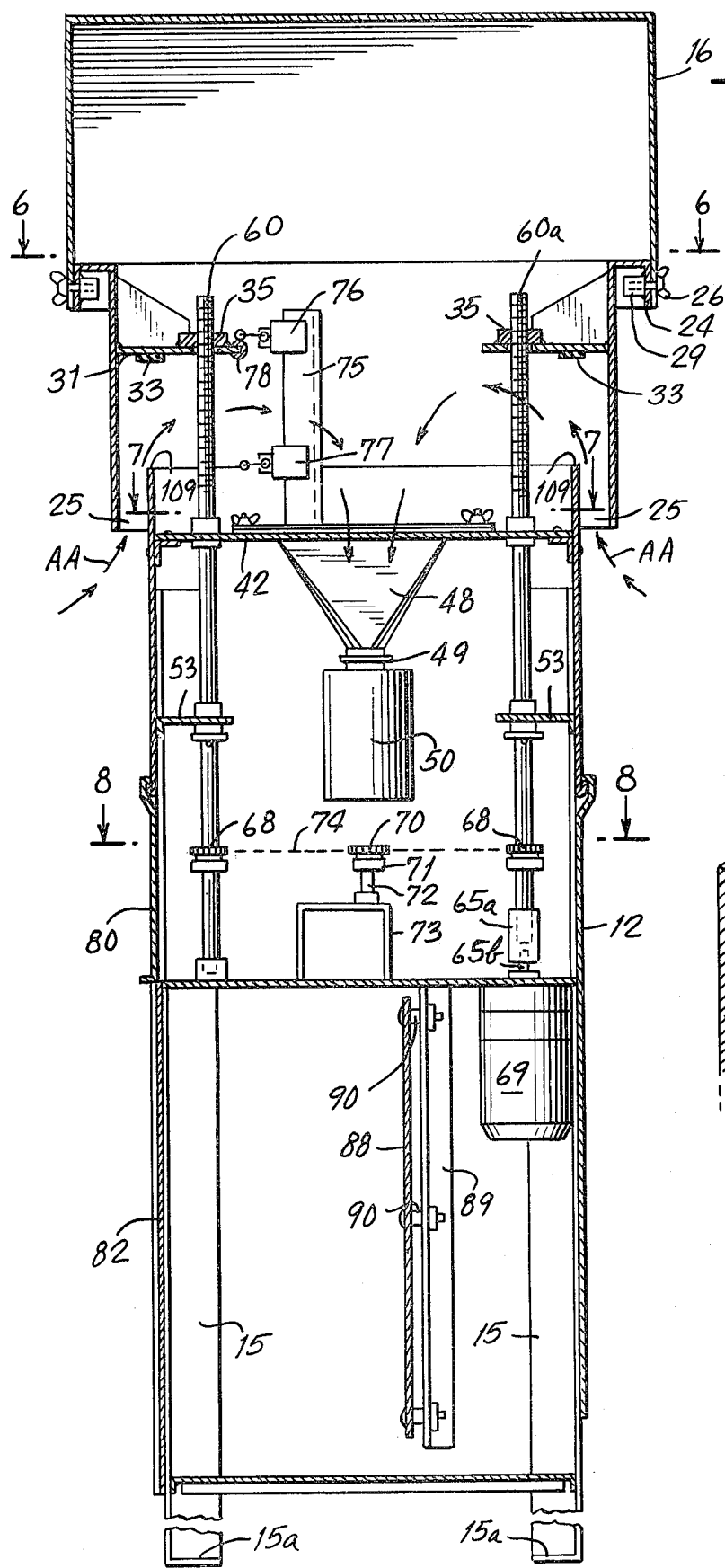
FIG. 4 is a longitudinal cross-sectional view similar to FIG. 3, showing the roof in its elevated position.
Figure 5:
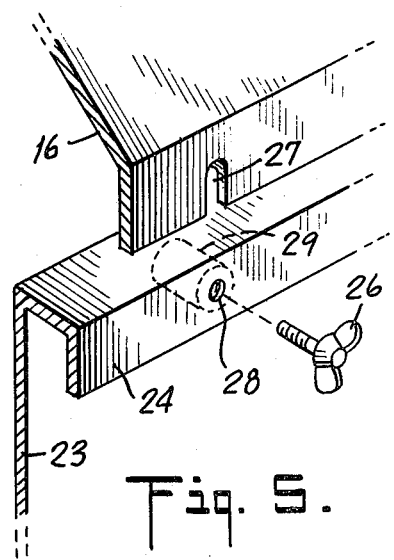
FIG. 5 is a fragmentary perspective view showing the means for removably fastening the gabled portion of the roof to a depending skirt portion.

Referring now to the drawings for a more complete understanding of the invention, it will be noted that the high volume air sampler comprises a rectangular structure 10 having four side walls 11, 12, 13, 14 which are suitably supported on the ground by legs 15 having inturned flanges 15a providing feet for the same. At the upper end of the structure 10 is a gabled roof 16 having two sloping top surfaces 17, 18, gabled ends 19, 20, and a depending skirt 23 also having four sides, the upper edges of which are joined to the lower roof edges. It will be noted that the gabled roof 16 and the skirt 23 are of larger cross-sectional dimension than the lower structure 10, so that both overhang the side walls 11, 12, 13, 14, and are spaced therefrom by an open area 25. The skirt 23 has at its upper end an outwardly and downwardly turned flange 24 which fits within the gabled roof 16 and is secured thereto by a plurality of wing nuts 26 going through downwardly opened end slots 27 in the gabled roof portion and matching holes 28 in the flange 24. An internally threaded bushing is secured to the inside surface of the flange,—the bushings and wing nuts when tightened serving to hold the gabled roof portion 17, 18, 19 and 20 in assembly with the skirt. By loosening the wing nuts the entire gabled roof portion may be lifted off the skirt portion to expose the underlying structure and mechanisms, so as to provide access for the insertion and removal of the filter paper, as well as to make adjustments and repairs to the internal mechanisms of the structure.

Secured to the inner faces of the skirt 23 near the upper end thereof is a horizontal supporting platform 31 which defines an open rectangular area between its four inner edges 32. A rubber gasket 33 is secured to the bottom face of the platform 31, said gasket being continuous and rectangular in plan view. There are also four holes 34 in the platform inwardly of each corner, each hole being provided on its top with an axially aligned nut 35 welded thereto. Gussets 37 are connected to the upper end of the skirt 23 and to the upper surface of platform 31 inwardly of the nuts 35.

Below the top of the side walls 11, 12, 13, 14 of the lower structure 10 is secured preferably by welding a right-angled member 40 which serves as a support for the filter deck 42. The filter deck occupies all of the space between the four walls, except that it has a rectangular opening therein over which the filter paper 43 is placed. As best seen in FIG. 7, the filter paper is clamped to the deck 42 by an open frame 44 having slots 45 for receiving bolts and wing nuts 46. Below the filter paper 43 is a conical filter holder 48 which at its small end is connected to the housing of a vacuum blower 49. The blower in turn is mounted on the housing of an electric motor 50 which rotates the blower to create a vacuum in the filter holder 48.

Outwardly of the open frame 44 there are four bushings 51 which are in vertical alignment with the nuts 35. Also further down on the walls there are arms 53 which support bushings 54. Below each bushing 54 is a thrust washer 55 which is held in place by a cotter pin 56 engaged in rod 60. A third bushing 61 is mounted on each rod 60 and secured thereto by a pin 62.

Four vertical rods 60 are each mounted in bushings 51, 54 and 61. The vertical rods 60 are screw-threaded at their upper ends 64 and screw-threadedly engage nuts 35. The lower end of each rod is mounted in a bearing block 65 supported on a platform 66 which is supported at each corner by the upper ends of right-angled legs 15. Thrust washers 55 prevent upward movement of rods 60 when rotated in engagement with nuts 35.

Each rod 60 has a sprocket 68 welded to it above bushing 61. One rod 60a has located below it a reduction gear and reversible motor combination 69 which is secured to platform 66. The shaft of the reduction gear and reversible motor combination is in vertical alignment with rod 60a and in driving connection therewith through bushing 65a and shaft extension 65b.

A fifth sprocket 70, bushing 71, and stub shaft 72 are mounted on a small raised platform 73,—such sprocket 70 serving as a tensioner for an endless chain 74 which engages all five sprockets to turn them in response to the reduction gear and reversible motor combination 69. As best seen in FIG. 8, the tensioning sprocket acts against the outside of the chain, whereas the other four sprockets engage the inside of the chain 74.

At the top of the lower structure 10 and extending into the roof area, there is a vertically disposed angled member 75 which is secured to the filter deck 42 exteriorly of the frame 44 as best shown in FIG. 6. The angled member has an upper limit switch 76 secured thereto and a lower limit switch 77 also secured thereto, each of said limit switches being adapted to be actuated by a trigger 78 mounted on horizontal platform 31.

It will be noted from FIG. 1 that the lower structure of the volume air sampler is in the form of a cabinet having two hinged doors on its front, the upper door 80 having a locking handle 81 and the lower door 82 having a locking handle 83. The door hinges are shown respectively at 84 and 85. There are three push buttons 79a, 79b, 79c, shown in the door 82, such push buttons, depending upon the wiring layout, being usable to move the roof to its up position, its down position, or on automatic control. There is also a service door on the back side of the cabinet. The cabinet also has mounted on its sides two handles 87, 87, for ease in lifting the structure for trans-shipment to another location.

As seen in FIGS. 3 and 4 there is a panel board 88 located within the cabinet behind the door 82 for mounting various electrical components. The panel board is suitably insulated from its mounting angled member 89 by insulators 90.

Figure 9:
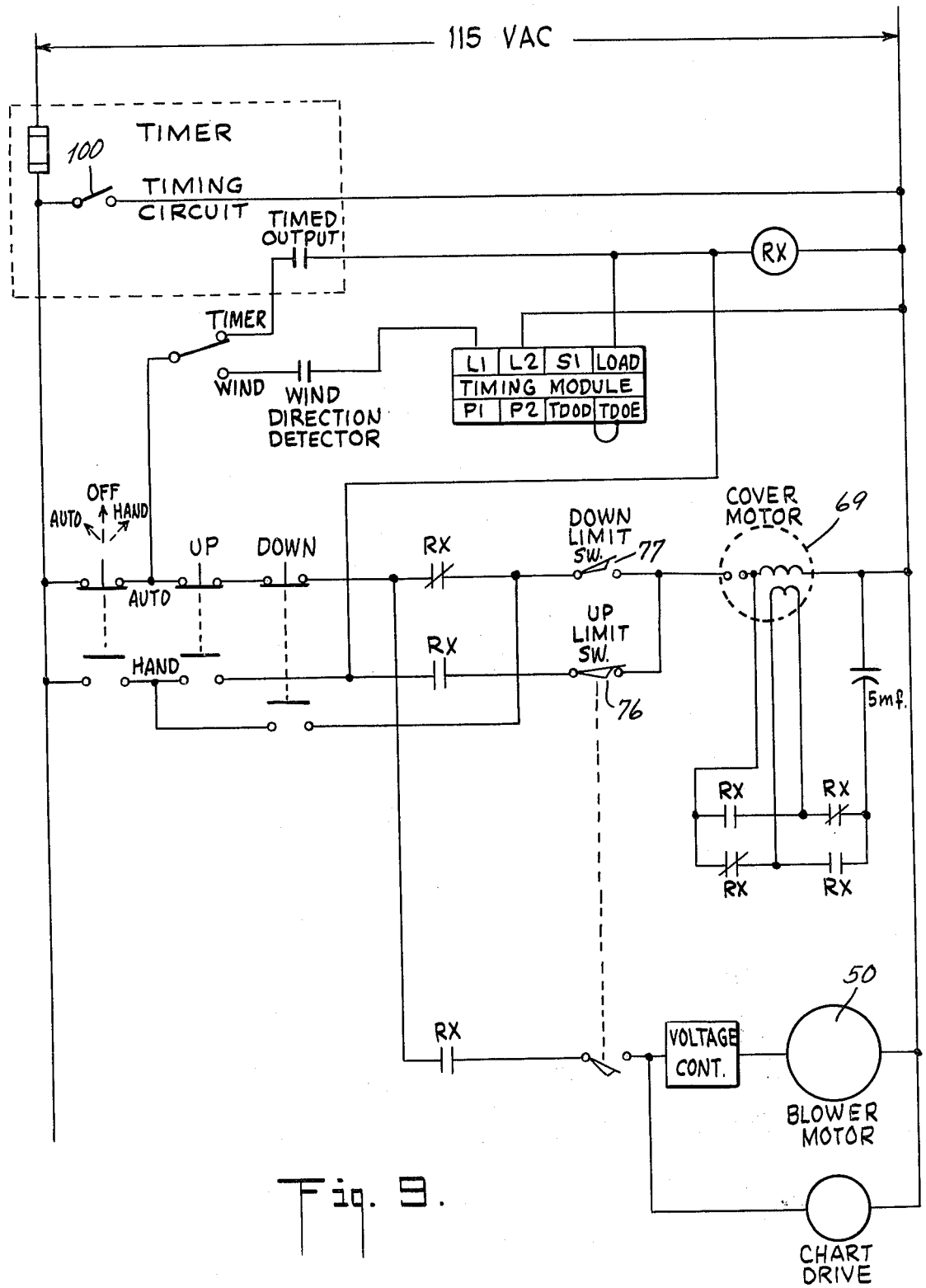
FIG. 9 is a schematic wiring diagram showing the essential components and circuitry of the electrical system forming part of the volume air sampler.

In FIG. 9 there is shown a schematic wiring diagram for the volume air sampler which shows the essential electrical components and the basic circuitry for the electrical system. From this diagram it will be understood that when voltage is applied the timer will be placed in circuit and that the timing circuit switch 100 will close at the start of a pre-set interval. The motor forming part of the reduction gear and reversible motor combination 69 will then operate and cause the roof to be moved upwardly from the position shown in FIG. 3 to the position shown in FIG. 4, at which time the upper limit switch 76 will be contacted and turn off motor 69. At the same time the blower 50 will be placed in circuit, thereby creating a vacuum in the conical filter holder 48 and causing air to be sucked in through the spaced 25 between the skirt 23 and the upper end of the cabinet,—the path of the air intake being shown by arrows A—A in FIG. 4.

At the end of the pre-set timer interval the timer circuit will open and turn off the blower motor and in turn will close another circuit which will cause the motor 69 to reverse its direction and the direction of the screw threaded rods 64 thereby lowering the roof until the gasket 33 is in sealing contact with the upper edge 109 of the cabinet structure thereby cutting off air access to the interior of the sampler. Simultaneously trigger 78 will actuate the lower limit switch 77 to turn off motor 69. Motor 50 will also be turned off.

At the end of the 6 day period or whatever other time is selected for sampling, the roof 16 is removed to give access to the filter paper. The filter paper with particulate is removed for observation and other determinations and a new filter paper is installed for another sampling.

In order to facilitate visualization of the high volume air sampler of the present invention it should be mentioned that in a typical embodiment the over-all height when the roof is in raised position is approximately 6½ feet.

What is claimed is:

1. A high volume air sampler comprising a structure housing a filter exposed to the air for collecting particulate from the air, a vacuum blower beneath said filter, and an electric circuit including a timer operatively connected to said vacuum blower for operating the same during a pre-set time interval, characterized in that said structure has a vertically movable roof which in its raised position exposes said filter to the air, and in its lowered position encloses the filter and excludes the admission of particulate to said filter.

2. A high volume air sampler according to claim 1, wherein said movable roof is supported on vertical rods having screw-threaded ends which engage in nuts secured to said roof, said rods in cooperation with said nuts upon rotation causing the roof to be raised or lowered with respect to said filter.

3. A high volume air sampler according to claim 1, wherein said movable roof is supported on vertical rods having screw-threaded ends which engage in nuts secured to said roof, each of said rods at its lower end having a sprocket secured thereon, one of said sprockets being a drive sprocket and mounted on the shaft of a reversible electric motor, and a continuous chain engaging said drive sprocket and said other sprockets, whereby upon energization of said motor the rods will rotate and raise or lower the roof.

4. A high volume air sampler according to claim 1, wherein the structure has a gabled roof and a skirt portion overlying and spaced from a cabinet portion, the cabinet portion having exposed upper edges, and wherein the vertically movable roof has a platform with a central open area and a gasket disposed on the under surface of said platform and arranged for sealing engagement with the upper edges of the cabinet when the roof is in lowered position, whereby the filter is sealed from exposure to more particulate.

5. A high volume air sampler according to claim 1, wherein said movable roof is supported on vertical rods having screw-threaded ends which engage in nuts secured to said roof, each of said rods at its lower end having a sprocket secured thereto, a drive sprocket mounted on the shaft of a reversible electric motor, and a continuous chain engaging said drive sprocket and said sprockets on said rods, the energization of the motor in one direction in turn rotating the rods to raise the roof, a limit switch trigger supported by the roof and engageable by an upper limit switch when the roof reaches its raised position to trip the same and to place the vacuum blower and motor in circuit to operate the same to facilitate collection of particulate from the air on the filter.

6. A high volume air sampler according to claim 1, wherein said movable roof is supported on vertical rods having screw-threaded ends which engage in nuts secured to said roof, each of said rods at its lower end having a sprocket secured thereto, one of said sprockets being a drive sprocket mounted on the shaft of a reversible electric motor, and a continuous chain engaging said drive sprocket and said other sprockets on said rods, the energization of the motor in one direction rotating the rods to raise the roof, and in the opposite direction rotating the rods to lower the roof, a limit switch trigger supported by the roof and engageable by an upper limit switch when the roof reaches its raised position to trip the same and to place the vacuum blower and motor in circuit to operate the same to facilitate collection of particulate from the air on the filter, and a lower limit switch engageable by the trigger when the roof is in its lowered position to break the circuit with the vacuum blower and motor to render same inoperative.

7. A high volume air sampler according to claim 1, wherein said movable roof is supported on vertical rods having screw-threaded ends which engage in nuts secured to said roof, each of said rods at its lower end having a sprocket secured thereto, one of said sprockets being a drive sprocket mounted on the shaft of a reversible electric motor, and a continuous chain engaging said drive sprocket and said other sprockets on said rods, said motor being in circuit with said timer and adapted to be energized at the start of the pre-set interval, the energization of the motor in one direction rotating the rods to raise the roof and in the opposite direction rotating the rods to lower the roof, a limit switch trigger supported by the roof and engageable by an upper limit switch when the roof reaches its raised position to trip the same and to place the vacuum blower and motor in circuit to operate the same to facilitate collection of particulate from the air on the filter, and a lower limit switch engageable by the trigger when the roof is in its lowered position to break the circuit with the vacuum blower and motor.

8. A high air volume sampler according to claim 1, wherein the roof is formed of a skirt portion and a gabled portion removably connected thereto to provide access to the structure interior to remove the filter with particulate and to replace the same.

9. A high volume air sampler comprising a structure housing a filter exposed to the air for collecting particulate from the air, a vacuum blower with electric motor beneath said filter, and an electric circuit including a timer operatively connected to said vacuum blower motor for operating the same during a pre-set time interval, characterized in that said structure has a vertically movable roof which in its raised position exposes said filter to the air, and in its lowered position encloses the filter, and electromechanical means in electric circuit with said timer which operate to raise the roof at the start of the pre-set time interval, and to lower the same at the end of said interval.

* * * * *